US00PP26601P2

(12) United States Plant Patent
Hokanson et al.

(10) Patent No.: US PP26,601 P2
(45) Date of Patent: Apr. 12, 2016

(54) ***RHODODENDRON* PLANT NAMED 'UMNAZ 502'**

(50) Latin Name: *Rhododendron hybrida*
Varietal Denomination: UMNAZ 502

(71) Applicants: Stan C. Hokanson, St. Paul, MN (US); Steve McNamara, Victoria, MN (US)

(72) Inventors: Stan C. Hokanson, St. Paul, MN (US); Steve McNamara, Victoria, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 167 days.

(21) Appl. No.: 13/999,113

(22) Filed: Jan. 14, 2014

(51) Int. Cl.
*A01H 5/02* (2006.01)

(52) U.S. Cl.
USPC ..... Plt./240

(58) Field of Classification Search
USPC ..... Plt./240
See application file for complete search history.

(56) References Cited

PUBLICATIONS

Hokanson. *Rhododendrons* et compagnie vol. 4, No. 3, 2012, pp. 1-11.*

SDL Free Translation and Professional Translation Service, retrieved on Aug. 19, 2015, retrieved from the Internet at <www.freetranslation.com/en/translate-english-french> translation of p. 8 of Hokanson reference, 2 pp.*

* cited by examiner

*Primary Examiner* — June Hwu
(74) *Attorney, Agent, or Firm* — Penny J. Aguirre

(57) ABSTRACT

A new cultivar of hybrid *Rhododendron* plant named 'UMNAZ 502' that is characterized by its irregularly rounded and compact plant habit reaching 1.4 m in height and width after 15 years of growth, its abundance of flowers that are dark red in color in mid to late May in Minnesota with the red color retained throughout the bloom period without substantial fading prior to abscission, its good cold hardiness with flower buds that are resistant to cold damage and consistently bloom even when exposed to temperatures as low as −30° F., and its good foliar tolerance to powdery mildew and other foliar diseases.

2 Drawing Sheets

STATEMENT REGARDING FEDERALLY SPONSORED RESEARCH

This invention was made with government support under MN-22-055 awarded by the U.S. Dept. of Agriculture. The government has certain rights in the invention.

Botanical classification: *Rhododendron hybrida.*

Cultivar designation: 'UMNAZ 502'.

BACKGROUND OF THE INVENTION

The present invention relates to a new and distinct cultivar of *Rhododendron* plant of hybrid origin, botanically known as *Rhododendron* hybrid 'UMNAZ 502' and will be referred to hereafter by its cultivar name, 'UMNAZ 502'. 'UMNAZ 502'is a new cultivar of deciduous *Rhododendron* grown for use as a landscape plant.

The new cultivar was developed through an on-going breeding program conducted by the Inventors in Excelsior, Minn. The objectives of the breeding program are to develop new cultivars of *Rhododendron* that exhibit cold tolerance, excellent floral displays, disease-resistant foliage, and compact, deciduous plant habits. The new cultivar was derived from a cross made by the Inventors on May 20, 1991 between *Rhododendron hybrida* 'UMNAZ393' (not patented), as the female parent, and *Rhododendron hybrida* 'UMNAZ394' (not patented), as the male parent. The Inventors selected 'UMNAZ 502' as a single unique plant amongst the seedlings that resulted from the above cross in June of 1995.

Asexual propagation of the new cultivar was first accomplished by softwood stem cuttings in Excelsior, Minn., USA in June 1995 by one of the Inventors. Asexual propagation by softwood stem cuttings and tissue culture has determined that the characteristics of the new cultivar are stable and are reproduced true to type in successive generations.

SUMMARY OF THE INVENTION

The following traits have been repeatedly observed and represent the characteristics 'UMNAZ 502'. These attributes in combination distinguish 'UMNAZ 502' as a new and distinct cultivar of *Rhododendron.*

1. 'UMNAZ 502' exhibits an irregularly rounded, compact plant habit, reaching 1.4 m in height and width after 15 years of growth.
2. 'UMNAZ 502' exhibits an abundance of flowers that are dark red in color in mid to late May in Minnesota with the red color retained throughout the bloom period without substantial fading prior to abscission.
3. 'UMNAZ 502' exhibits good cold hardiness with flower buds that are resistant to cold damage and consistently bloom even when exposed to temperatures as low as −30° F.
4. 'UMNAZ 502' exhibits foliage with tolerance to powdery mildew and other foliar diseases.

The female parent of 'UMNAZ 502', 'UMNAZ393', differs from 'UMNAZ 502' in having a less compact plant habit with more open branching, in having flowers that fade to a pale red prior to abscission, and in having fewer flower buds. The male parent, 'UMNAZ394', differs from 'UMNAZ 502' in having flowers that are orange-red in color with an orange-gold patch on the top petal, and in being more susceptible to powdery mildew. 'UMNAZ 502' can also be most closely compared to the *Rhododendron* cultivars 'Arneson Flame' (not patented) and 'Arneson Ruby Princess' (not patented). Both are similar to 'UMNAZ 502' in being deciduous and in having flowers that are red in color. Both differ from 'UMNAZ 502' in having flower buds and stems that are less cold tolerant in U.S.D.A. Zone 4 winters.

BRIEF DESCRIPTION OF THE DRAWINGS

The accompanying colored photographs were taken of a 21 year-old plant of the new cultivar as grown outdoors in an evaluation nursery in Excelsior, Minn.

The photograph in FIG. 1 provides a view of the overall plant habit of 'UMNAZ 502' in bloom.

Figure 1:
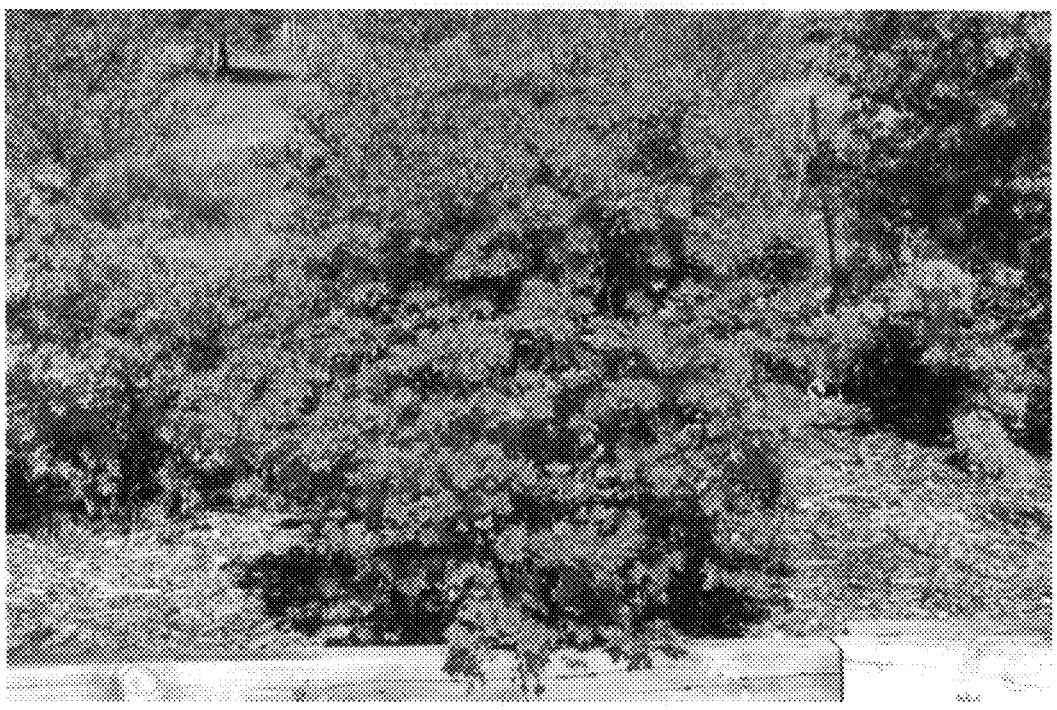
Figure 2:
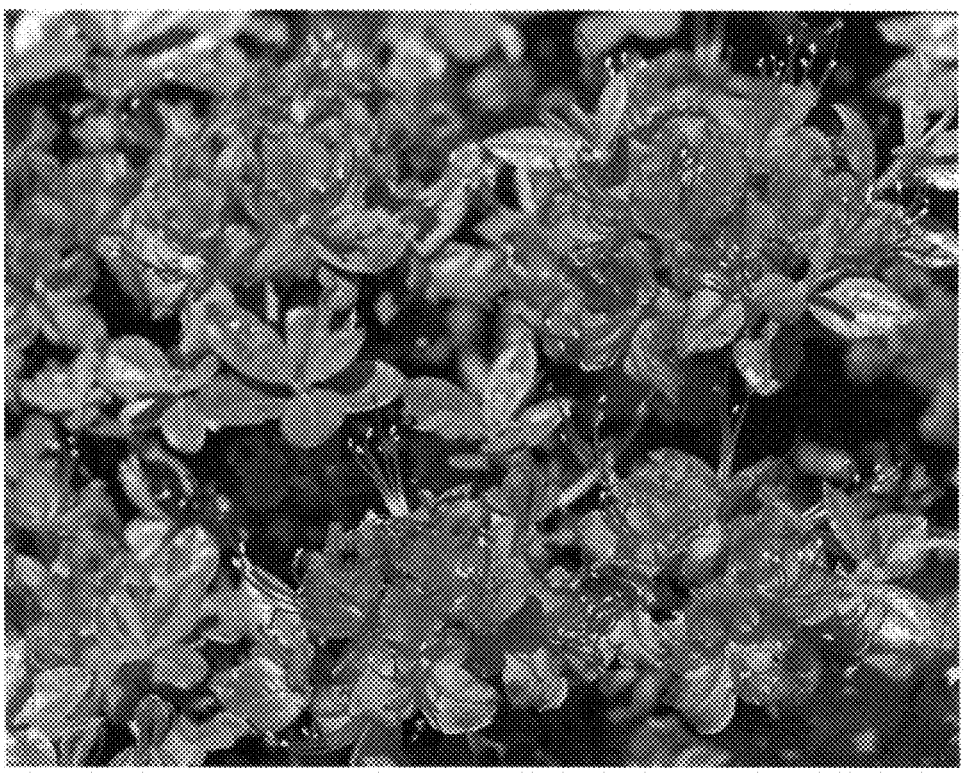

The photograph in FIG. 2 provides a close-up view of the inflorescences of 'UMNAZ 502'.

Figure 3:
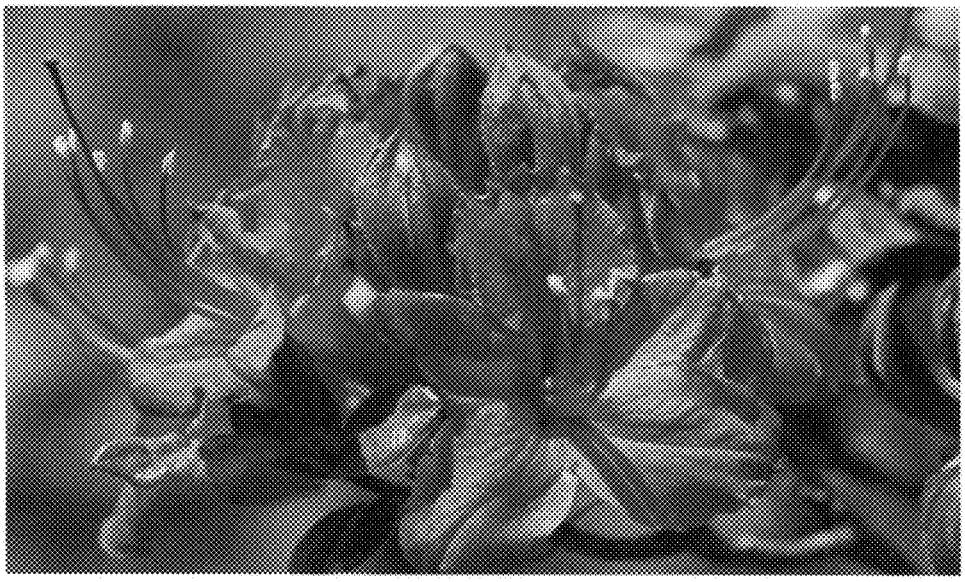

The photograph in FIG. 3 provides a close-up view of the flowers of 'UMNAZ 502'.

The colors in the photographs are as close as possible with the digital photography and printing techniques utilized and the color codes in the detailed botanical description accurately describe the new *Rhododendron.*

DETAILED BOTANICAL DESCRIPTION OF THE PLANT

The following is a detailed description of 21 year-old plants of the new cultivar as grown outdoors in an evaluation nursery in Excelsior, Minn. The plants were grown in day temperatures ranging from −21° to 39° C. and night temperatures ranging from −38° to 24° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General characteristics:

*Blooming period.*—2 to 3 weeks in late May to early June in Chanhassen, Minn.

*Plant type.*—Deciduous shrub.

*Plant habit.*—Compact, upright, irregularly-rounded, and densely branched.

*Height and spread.*—Reaches 1.4 m in height and spread.

*Cold hardiness.*—At least to U.S.D.A. Zone 4a, flower buds are resistant to cold damage when exposed to temperatures down to −30° F.

*Diseases.*—Foliage has been observed to have tolerance to powdery mildew and other foliar diseases.

*Root description.*—Shallow and fibrous.

*Propagation.*—Tissue culture (preferred) or softwood stem cuttings.

*Growth rate.*—Slow to moderate.

Stem description:

*Shape.*—Round.

*Stem color.*—New growth; a blend of 144D and 145A, mature wood; 202A to 202C, dormant wood; 164A.

*Stem size.*—Main stems; an average of 10.5 cm in length and 3 mm in width.

*Stem surface.*—New growth; lightly pubescent, mature wood; glabrous.

*Stem aspect.*—Held at an average angle of 25° (0°=vertical).

*Branching.*—Self-branching.

Foliage description:

*Leaf shape.*—Elliptical.

*Leaf division.*—Simple.

*Leaf base.*—Cuneate.

*Leaf apex.*—Acute to acuminate.

*Leaf venation.*—Pinnate, upper surface 146A in color, and lower surface 144B to 144C in color with short hairs along the midrib 0.5 mm in length and N155A in color.

*Leaf margins.*—Entire and fringed with short hairs 0.5 mm in length and NN155D in color.

*Leaf attachment.*—Petiolate.

*Leaf arrangement.*—Alternate.

*Leaf orientation.*—Held horizontal to upright.

*Leaf aspect.*—Cupped downward.

*Leaf surface.*—Upper surface; smooth, glabrous and glossy, lower surface; smooth, glabrous with short hairs along midrib 0.5 mm in length N155A in color.

*Leaf color.*—Young leaves upper surface 146C, lower surface; 146B to 146C, mature leaves upper surface; 146A and 147A and suffused with 184B in spring, mature leaves lower surface; 147B, fall color; upper surface;187B and 187C, lower surface; 186D.

*Leaf size.*—Average of 3.7 cm in length, and 2.1 cm in width.

*Leaf quantity.*—An average of 12 leaves per lateral branch 10.5 cm in length.

*Petioles.*—Average of 5 mm in length and 1.5 mm in diameter, 144C in color, glabrous and lightly pubescent surface.

Flower description:

*Inflorescence type.*—Umbellate raceme.

*Lastingness of flowers.*—An average 9 days, mostly self-cleaning.

*Inflorescence size.*—6 to 8 cm in height and 8 to 12 cm in width.

*Flower size.*—An average of 3 cm in depth and 4.5 cm in diameter.

*Flower fragrance.*—None.

*Flower shape.*—Broad tubular funnel.

*Flower number.*—An average of 18 per lateral stem.

*Flower aspect.*—Outward.

*Flower bud.*—Obovate in shape, an average of 9.5 mm in depth and 5 mm in diameter, apex; acute, summer color; a color between 144C and 151C with 165B near the apex, winter color; 175C.

*Flower attachment.*—Pedicel.

*Petal number.*—5.

*Petal shape.*—Elliptic and sometimes recurved.

*Petal color.*—Upper surface when opening; 45A, lower surface when opening 53B, upper surface when fully open 45A marbled with 46B, lower surface when fully open 44A, color fades to 53C on both surfaces.

*Petal surface.*—Upper surface; glabrous, smooth to slightly rugose, lower surface; smooth, glabrous except for moderate pubescence along medial axis.

*Petal margins.*—Entire and undulate.

*Petal apex.*—Rounded to obtuse.

*Petal base*.—Fused.

*Petal size*.—Average of 2.3 cm in length and 1.5 cm in width.

*Sepal number*.—5.

*Sepal shape*.—Oblong.

*Sepal margin*.—Entire fringed with hairs 2 mm in length and NN155D in color.

*Sepal size*.—Average of 1 mm in length and 1.5 mm in width.

*Sepal arrangement*.—Forming a shallow cup around corolla tube base.

*Sepal surface*.—Pubescent on upper and lower surface.

*Sepal apex*.—Obtuse to rounded.

*Sepal base*.—Fused.

*Sepal color*.—Immature upper surface; (not visible) enclosing base of the corolla tube, immature lower surface; 145A, mature upper surface; 144B, mature lower surface a blend of 145A and 146D.

*Calyx*.—Shallow cup shape, an average of 2.5 mm in length and 3.5 mm in diameter.

*Pedicels*.—An average of 11 mm in length and 1.5 mm in diameter, smooth and lightly pubescent surface, 146C in color.

Reproductive organs:

*Gynoecium*.—1 Pistil, 5.5 cm in length, stigmas; circular, convex, and dome-shaped, 187B in color, style; an average of 5 cm in length and a blend of 44A to 45A in color, ovary; 146C in color.

*Androecium*.—Stamens; average of 5, anthers; oblong to elliptical in shape, 2.5 mm in length and 1.5 mm in width, 164C to 164D in color; pollen is moderate in quantity and 155D in color.

*Fruit/seeds*.—Seed capsule; an average of 20 mm in length and 7.5 mm in width, exterior 166A and interior 167C to 167D in color, fruit; an average of 1.7 cm in length and 5 mm in diameter, 146D in color, seed; an average of 3 mm in length and 1.5 mm in width, 164A and 166C in color, 50 to 150 seeds per capsule.

It is claimed:

1. A new and distinct cultivar of *Rhododendron* plant named 'UMNAZ 502' as herein illustrated and described.

* * * * *